US006300059B1

(12) United States Patent
Vogelstein et al.

(10) Patent No.: US 6,300,059 B1
(45) Date of Patent: Oct. 9, 2001

(54) CANCER DIAGNOSIS AND WAF1

(75) Inventors: Bert Vogelstein; Kenneth W. Kinzler, both of Baltimore, MD (US)

(73) Assignee: Johns Hopkins University, Baltimore, MD (US)

( * ) Notice: Subject to any disclaimer, the term of this patent is extended or adjusted under 35 U.S.C. 154(b) by 0 days.

(21) Appl. No.: 08/456,297

(22) Filed: Jun. 1, 1995

Related U.S. Application Data

(62) Division of application No. 08/149,829, filed on Nov. 10, 1993, now abandoned.

(51) Int. Cl.[7] .......................... C12Q 1/68; G01N 33/574

(52) U.S. Cl. .............................. 435/6; 435/7.1; 435/7.23; 436/64; 436/501

(58) Field of Search ................................ 435/6, 7.1, 7.23; 436/501, 64

(56) References Cited

U.S. PATENT DOCUMENTS

| | | | |
|---|---|---|---|
| 5,302,706 | 4/1994 | Smith | 536/23.1 |
| 5,596,079 * | 1/1997 | Smith et al. | 530/328 |

FOREIGN PATENT DOCUMENTS

| | | |
|---|---|---|
| WO 92/13091 | 8/1992 | (WO) . |
| PCT/US92/10904 | 12/1992 | (WO) . |
| WO 93/12251 | 6/1993 | (WO) . |

OTHER PUBLICATIONS

El–Deiry et al., "WAF1, a Potential Mediator of p53 Tumor Suppression", *Cell 75*:817–825 (1993).

Xiong et al., "p21 is a Universal Inhibitor of Cyclin Kinases", *Nature 366*:701–704 (1993).

Harper et al., "The p21 Cdk–Interacting Protein Cip1 is a Potent Inhibitor of G1 Cyclin–Dependent Kinases", *Cell 75*:805–816 (1993).

* cited by examiner

*Primary Examiner*—Kenneth R. Horlick
(74) *Attorney, Agent, or Firm*—Banner & Witcoff

(57) ABSTRACT

A human gene, WAF1, has been identified which is induced by wild-type but not mutant p53 in human brain tumor cells. The gene is located on chromosome 6p21.2 and directs the synthesis of an 18.1 kd protein. Introduction of WAF1 cDNA suppresses growth of human brain and colon tumor cells. The WAF1 gene and protein are useful inter alia for diagnosis and treatment of human tumors.

6 Claims, 13 Drawing Sheets

FIG. 3A

```
  1 GCC GAA GTC AGT TCC TTG TGG AGC CGG AGC TGG GCG CGG ATT CGC CGA

 49 GGC ACC GAG GCA CTC AGA GGA GGC GCC ATG TCA GAA CCG GCT GGG GAT
  1                                     Met Ser Glu Pro Ala Gly Asp

 97 GTC CGT CAG AAC CCA TGC GGC AGC AAG GCC TGC CGC CGC CTC TTC GGC
  8 Val Arg Gln Asn Pro Cys Gly Ser Lys Ala Cys Arg Arg Leu Phe Gly

145 CCA GTG GAC AGC GAG CAG CTG AGC CGC GAC TGT GAT GCG CTA ATG GCG
 24 Pro Val Asp Ser Glu Gln Leu Ser Arg Asp Cys Asp Ala Leu Met Ala

193 GGC TGC ATC CAG GAG GCC CGT GAG CGA TGG AAC TTC GAC TTT GTC ACC
 40 Gly Cys Ile Gln Glu Ala Arg Glu Arg Trp Asn Phe Asp Phe Val Thr

241 GAG ACA CCA CTG GAG GGT GAC TTC GCC TGG GAG CGT GTG CGG GGC CTT
 56 Glu Thr Pro Leu Glu Gly Asp Phe Ala Trp Glu Arg Val Arg Gly Leu

289 GGC CTG CCC AAG CTC TAC CTT CCC ACG GGG CCC CGG CGA GGC CGG GAT
 72 Gly Leu Pro Lys Leu Tyr Leu Pro Thr Gly Pro Arg Arg Gly Arg Asp

337 GAG TTG GGA GGA GGC AGG CGG CCT GGC ACC TCA CCT GCT CTG CTG CAG
 88 Glu Leu Gly Gly Gly Arg Arg Pro Gly Thr Ser Pro Ala Leu Leu Gln

385 GGG ACA GCA GAG GAA GAC CAT GTG GAC CTG TCA CTG TCT TGT ACC CTT
104 Gly Thr Ala Glu Glu Asp His Val Asp Leu Ser Leu Ser Cys Thr Leu

433 GTG CCT CGC TCA GGG GAG CAG GCT GAA GGG TCC CCA GGT GGA CCT GGA
120 Val Pro Arg Ser Gly Glu Gln Ala Glu Gly Ser Pro Gly Gly Pro Gly

481 GAC TCT CAG GGT CGA AAA CGG CGG CAG ACC AGC ATG ACA GAT TTC TAC
136 Asp Ser Gln Gly Arg Lys Arg Arg Gln Thr Ser Met Thr Asp Phe Tyr

529 CAC TCC AAA CGC CGG CTG ATC TTC TCC AAG AGG AAG CCC TAA TCC GCC
152 His Ser Lys Arg Arg Leu Ile Phe Ser Lys Arg Lys Pro ***
```

FIG. 3B

577 CAC AGG AAG CCT GCA GTC CTG GAA GCG CGA GGG CCT CAA AGG CCC GCT
625 CTA CAT CTT CTG CCT TAG TCT CAG TTT GTG TGT CTT AAT TAT TAT TTG
673 TGT TTT AAT TTA AAC ACC TCC TCA TGT ACA TAC CCT GGC CGC CCC CTG
721 CCC CCC AGC CTC TGG CAT TAG AAT TAT TTA AAC AAA AAC TAG GCG GTT
769 GAA TGA GAG GTT CCT AAG AGT GCT GGG CAT TTT TAT TTT ATG AAA TAC
817 TAT TTA AAG CCT CCT CAT CCC GTG TTC TCC TTT TCC TCT CTC CCG GAG
865 GTT GGG TGG GCC GGC TTC ATG CCA GCT ACT TCC TCC TCC CCA CTT GTC
913 CGC TGG GTG GTA CCC TCT GGA GGG GTG TGG CTC CTT CCC ATC GCT GTC
961 ACA GGC GGT TAT GAA ATT CAC CCC CTT TCC TGG ACA CTC AGA CCT GAA
1009 TTC TTT TTC ATT TGA GAA GTA AAC AGA TGG CAC TTT GAA GGG GCC TCA
1057 CCG AGT GGG GGC ATC ATC AAA AAC TTT GGA GTC CCC TCA CCT CCT CTA
1105 AGG TTG GGC AGG GTG ACC CTG AAG TGA GCA CAG CCT AGG GCT GAG CTG
1153 GGG ACC TGG TAC CCT CCT GGC TCT TGA TAC CCC CCT CTG TCT TGT GAA
1201 GGC AGG GGG AAG GTG GGG TAC TGG AGC AGA CCA CCC CGC CTG CCC TCA
1249 TGG CCC CTC TGA CCT GCA CTG GGG AGC CCG TCT CAG TGT TGA GCC TTT
1297 TCC CTC TTT GGC TCC CCT GTA CCT TTT GAG GAG CCC CAG CTT. ACC CTT
1345 CTT CTC CAG CTG GGC TCT GCA ATT CCC CTC TGC TGC TGT CCC TCC CCC
1393 TTG TCT TTC CCT TCA GTA CCC TCT CAT GCT CCA GGT GGC TCT GAG GTG
1441 CCT GTC CCA CCC CCA CCC CCA GCT CAA TGG ACT GGA AGG GGA AGG GAC
1489 ACA CAA GAA GAA GGG CAC CCT AGT TCT ACC TCA GGC AGC TCA AGC AGC
1537 GAC CGC CCC CTC CTC TAG CTG TGG GGG TGA GGG TCC CAT GTG GTG GCA
1585 CAG GCC CCC TTG AGT GGG GTT ATC TCT GTG TTA GGG GTA TAT GAT GGG
1633 GGA GTA GAT CTT TCT AGG AGG GAG ACA CTG GCC CCT CAA ATC GTC CAG
1681 CGA CCT TCC TCA TCC ACC CCA TCC CTC CCC AGT TCA TTG CAC TTT GAT
1729 TAG CAG CGG AAC AAG GAG TCA GAC ATT TTA AGA TGG TGG CAG TAG AGG
1777 CTA TGG ACA GGG CAT GCC ACG TGG GCT CAT ATG GGG CTG GGA GTA GTT
1825 GTC TTT CCT GGC ACT AAC GTT GAG CCC CTG GAG GCA CTG AAG TGC TTA
1873 GTG TAC TTG GAG TAT TGG GGT CTG ACC CCA AAC ACC TTC CAG CTC CTG
1921 TAA CAT ACT GGC CTG GAC TGT TTT CTC TCG GCT CCC CAT GTG TCC TGG
1969 TTC CCG TTT CTC CAC CTA GAC TGT AAA CCT CTC GAG GGC AGG GAC CAC
2017 ACC CTG TAC TGT TCT GTG TCT TTC ACA GCT CCT CCC ACA ATG CTG AAT
2065 ATA CAG CAG GTG CTC AAT AAA TGA TTC TTA GTG ACT TTA AAA AAA AAA
2113 AAA AAA AAA

FIG. 7A

```
1                                                 Met Ser Asn Pro Gly Asp Val     7
     CT TCT TGT GTT TCA GCC ACA GGC ACC ATG TCC AAT CCT GGT GAT GTC

8    Arg Pro Val Pro His Arg Ser Lys Val Cys Arg Cys Leu Phe Gly Pro     23
     CGA CCT GTT CCG CAC AGG AGC AAA GTG TGC CGT TGT CTC TTC GGT CCC

24   Val Asp Ser Glu Gln Leu Ser Arg Asp Cys Asp Ala Leu Met Ala Gly     39
     GTG GAC AGT GAG CAG TTG AGC CGT GAT TGC GAT GCG CTC ATG GCG GGC

40   Cys Leu Gln Glu Ala Arg Glu Arg Trp Asn Phe Asp Phe Val Thr Glu     55
     TGT CTC CAG GAG GCC CGA GAA CGG TGG AAC TTT GAC TTC GTC ACG GAG

56   Arg Gln Leu Glu Gly Asn Phe Val Trp Glu Arg Val Arg Ser Leu Gly     71
     AGG CAG CTG GAG GGC AAC TTC GTC TGG GAG CGC GTT CGG AGC CTA GGG

72   Leu Pro Lys Val Tyr Leu Ser Pro Gly Ser Arg Ser Arg Asp Asp Leu     87
     CTG CCC AAG GTC TAC CTG AGC CCT GGG TCC CGC AGC CGT GAC GAC CTG

88   Gly Gly Asp Lys Arg Pro Ser Thr Ser Ser Ala Leu Leu Gln Gly Pro     103
     GGA GGG GAC AAG AGG CCC AGT ACT TCC TCT GCC CTG CTG CAG GGG CCA

04   Ala Pro Glu Asp His Val Ala Leu Ser Leu Ser Cys Thr Leu Val Ser     119
     GCT CCG GAG GAC CAC GTG GCC TTG TCG CTG TCT TGC ACT CTG GTG TCT

20   Glu Arg Pro Glu Asp Ser Pro Gly Gly Pro Gly Thr Ser Gln Gly Arg     135
     GAG CGG CCT GAA GAT TCC CCG GGT GGG CCC GGA ACA TCT CAG GGC CGA

36   Lys Arg Arg Gln Thr Ser Leu Thr                                     143
     AAA CGG AGG CAG ACC AGC CTG ACA GGT AAG GAC AGG AGC AGA GAA GGA
```

FIG. 7B

```
               10        20        30        40        50        60
Human  MSEPAGDVRQNPCGSKACRRLFGPVDSEQLSRDCDALMAGCIQEARERWNFDFVTETPLE
       || | ||||  |  ||.|| |||||||||||||||||||||.||||||||||||||  ||
Mouse  MSNP-GDVRPVPHRSKVCRCLFGPVDSEQLSRDCDALMAGCLQEARERWNFDFVTERQLE
                10        20        30        40        50

               70        80        90       100       110       120
Human  GDFAWERVRGLGLPKLYLPTGPRRGRDELGGGRRPGTSPALLQGTAEEDHVDLSLSCTLV
       | |.||||| |||||.||  |  | ||.||| .|| || ||||| | |||| ||||||||
Mouse  GNFVWERVRSLGLPKVYLSPGS-RSRDDLGGDKRPSTSSALLQGPAPEDHVALSLSCTLV
     60        70        80         90       100       110

              130       140
Human  PRSGEQAEGSPGGPGDSQGRKRRQTSMT
          |  | |||||| |||||||||| |
Mouse  ---SERPEDSPGGPGTSQGRKRRQTSLT
        120       130       140
```

CANCER DIAGNOSIS AND WAF1

This application is a division of application Ser. No. 08/149,829, filed Nov. 10, 1993, abandoned.

This invention was made with support from NIH grant CA 0907 and CA 43460. The U.S. government therefore retains some rights in the invention.

TECHNICAL FIELD

The invention relates to the fields of diagnosis and therapy of cancers. More particularly, the invention relates to a protein which can suppress tumor cell growth.

BACKGROUND OF THE INVENTION

Inactivation of p53 is a common event in the development of human neoplasia (Hollstein et al. (1991) *Science* 253, 49–53). A variety of mechanisms can lead to such functional inactivation, including p53 point mutations of deletions of p53 (Baker et al. (1989) *Science* 244, 217–221; Wolf, D., and Rotter, V. (1985) *Proc. Natl. Acad. Sci. USA* 82, 790–794), and interaction with oncogenic viral or cellular proteins (Mietz et al. (1992) *EMBO J.* 11, 5013–5020; Momand et al. (1992) *Cell* 69, 1237–1245). Wild-type p53 has been shown to be a suppressor of tumor cell growth (for reviews see Mercer, W. E. (1992) *Crit. Rev. Eucar. Gene Exp.* 2, 251–263; Oren, M. (1992) *FASEB J.* 6, 3169–3176; Lane, D. P. (1992) *Nature* 358, 15–16; Perry, M. E., and Levine, A. J. (1993) *Curr. Opin. in Genet. and Devel.* 3, 50–54). Inactivation of p53 by any of the above mechanisms thereby leads to a selective growth advantage, generally observed as tumor progression.

The mechanism underlying p53 growth suppression is still undefined. Several biochemical features of p53 have been elucidated, and at least two of these are currently of much interest. First, p53 has been shown to transcriptionally suppress a variety of promoters containing TATA-elements (Ginsberg et al. (1991) *Proc. Natl. Acad. Sci. USA* 88, 9979–9983; Santhanam et al. (1991) *Proc. Natl. Acad. Sci. USA* 88, 7605–7609; Kley et al. (1992) *Nucl. Acids Res.* 20, 4083–4087; Mack et al. (1993) *Nature* 363, 281–283). This suppression is apparently sequence independent, and may involve p53 binding to tie TATA-binding protein (TBP) or to other transcription factors (Seto et al. (1992) *Proc. Natl. Acad. Sci. USA* 89, 12028–12032; Truant et al. (1993) *J. Biol. Chem.* 268, 2284–2287; Ragimov et al. (1993) *Oncogene* 8, 1183–1193; Martin et al. (1993) *J. Biol. Chem.* 268, 13062–13067; Liu et al. (1993) *Mol. and Cell. Biol.* 13, 3291–3300). Second, p53 can bind to DNA in a sequence-specific manner (Kern et al. (1991) *Science* 252, 1707–1711). A 20 bp consensus binding site, consisting of two copies of the 10 bp sequence 5'-RRRCWWGYYY-3', separated by up to 13 bp, has been identified (El-Deiry et al. (1992) *Nature Genet.* 1, 45–49; Funk et al. (1992) *Mol. Cell. Biol.* 12, 2866–2871). Both copies of the 10 bp sequence are required for efficient binding by p53. p53 contains a strong transcriptional activation sequence near its amino terminus (Fields, S., and Jang, S. K. (1990) *Science* 249, 1046–1049; Raycroft et al. (1990) *Science* 249, 1049–1051), and can stimulate the expression of genes downstream of its binding site. Such stimulation has been demonstrated in both mammalian (Kern et al. (1992) Science 256, 827–830; Funk et al. (1992) *Mol. Cell. Biol.* 12, 2866–2871; Zambetti et al. (1992) *Gen. and Devel.* 6, 1143–1152) and yeast cells (Scharer, E., and Iggo, R. (1992) *Nucl. Acids Res.* 20, 1539–1545; Kern et al. (1992) *Science* 256, 827–830) as well as in an in vitro system (Farmer et al. (1992) *Nature* 358, 83–86).

The sequence-specific transcriptional activation by p53 has led to the hypothesis that p53-induced genes may mediate its biological role as a tumor suppressor (Pietenpol et al. (1993) *Cell* (submitted)). To date, several genes containing p53-binding sites have been identified. These include muscle creatine kinase (M C K, Weintraub et al. (1991) *Proc. Natl. Acad. Sci. USA* 88, 4570–4574; Zambetti et al. (1992) *Gen. and Devel.* 6, 1143–1152), GADD45 (Kastan et al. (1992) *Cell* 71, 587–597), MDM2 (Barak et al. (1993) *EMBO* 12, 461–468; Wu et al. (1993) *Genes and Devel.* 7, 1126–1132), and a GLN retroviral element (Zauberman et al. (1993) *EMBO J.* 12, 2799–2808). Each of these genes contains a 20 bp sequence with high homology to the p53 consensus binding site (Prives, C., and Manfredi, J. J. (1993) *Gen. and Devel.* 7, 529–534). The p53-binding sites in GADD45 and MDM2 are located within introns, the MCK site is 3 kb upstream of the transcription start site, and the GLN element is located within an LTR. The relationship of any of these genes to suppression of cell growth by p53 remains unclear. It has been suggested that MDM2 may be a feedback regulator of p53 action, by being transcriptionally induced (Barak et al. (1993) *EMBO* 12, 461–468; Wu et al. (1993) *Genes and Devel.* 7, 1126–1132), then inhibiting p53 function (Momand et al. (1992) *Cell* 69, 1237–1245; Oliner et al. (1993) *Nature* 362, 857–860; Wu et al. (1993) *Genes and Devel.* 7, 1126–1132). In this regard, MDM2 functions as an oncogene rather than as a tumor suppressor gene (Fakharzadeh et al. (1991) *EMBO J.* 10, 1565–1569; Finlay, C. A. (1993) *Mol. and Cell. Biol.* 13, 301–306).

There is a need in the art for elucidation of the pathway by which p53 exerts its tumor suppressive effects. There is also a need in the art for new diagnostic and therapeutic tools for evaluating and ameliorating human cancers.

SUMMARY OF THE INVENTION

It is an object of the invention to provide DNA molecules useful for diagnosing and treating human tumors.

It is another object of the invention to provide proteins useful for treating human tumors and for raising diagnostically useful antibodies.

It is still another object of the invention to provide antibodies which are useful for diagnosing human cancer.

It is yet another object of the invention to provide methods of suppressing growth of tumor cells.

It is an object of the invention to provide a method for screening potential therapeutic agents for treating cancer.

It is another object of the invention to provide methods for diagnosing cancer.

It is yet another object of the invention to provide a reporter construct, useful for screening potential antineoplastic agents.

It is an additional object of the invention to provide an antisense construct for inhibiting expression of a tumor suppressor gene.

It is still another object of the invention to provide antisense oligonucleotides for inhibiting expression of a tumor suppressor gene.

It is yet another object of the invention to provide methods for promoting growth of cells in which a tumor suppressor gene's expression is inhibited.

It is another object of the invention to provide a method for assessing susceptibility to cancers.

These and other objects of the invention are provided by one or more of the embodiments described below. In one embodiment of the invention an isolated and purified subchromosomal DNA molecule is provided. The molecule encodes WAF1 protein as shown in SEQ ID NO: 2, and contains three exons of 168 bp, 450 bp and 1600 bp. The sequence of said exons is shown in SEQ ID NO: 1.

In another embodiment of the invention an isolated and purified WAF1 protein is provided. The protein has a sequence as shown in SEQ ID NO: 2.

In yet another embodiment of the invention an antibody is provided. The antibody is specifically reactive with human WAF1 protein.

In still another embodiment of the invention a method of suppressing growth of tumor cells is provided. The method comprises administration of a WAF1 protein having a sequence as shown in SEQ ID NO: 2 to said cells.

In an additional embodiment of the invention a method of suppressing growth of tumor cells is provided. The method comprises administration to said cells of a DNA molecule which causes said cells to express WAF1, said DNA molecule having a sequence as shown in SEQ ID NO: 1.

According to another embodiment of the invention a method for screening potential therapeutic agents for the ability to suppress the growth of tumor cells by activating the expression of WAF1 is provided. The method comprises incubation of a potential therapeutic agent with a cell which contains a WAF1 reporter construct, said reporter construct comprising a WAF1 transcription regulatory region covalently linked in a cis configuration to a gene encoding an assayable product. Further, the method comprises measurement of the production of the assayable product. A potential therapeutic agent is identified as useful if it increases the production by the cell of the assayable product.

In still another embodiment of the invention a method for diagnosing cancer is provided. The method comprises testing a tissue to determine if the tissue expresses less WAF1 than normal tissue.

In another embodiment of the invention a method for diagnosing cancer is provided. The method comprises testing a tissue to determine if DNA in said tissue contains a mutant WAF1 gene.

In still another embodiment of the invention a WAF1 reporter construct is provided. The reporter construct comprises a WAF1 transcription regulatory region covalently linked in a cis configuration to a gene encoding an assayable product.

In another embodiment of the invention an antisense WAF1 construct is provided. The construct comprises: a transcriptional promoter; a transcriptional terminator; and a DNA segment comprising one or more segments of the WAF1 gene, said gene segment located between said promoter and said terminator, said DNA segment being inverted with respect to said promoter and said terminator, whereby RNA produced by transcription of the DNA segment is complementary to a corresponding segment of WAF1 RNA produced by human cells.

In another embodiment of the invention a WAF1 antisense oligonucleotide is provided. The oligonucleotide comprises at least ten nucleotides complementary to a sequence present in WAF1 mRNA.

In yet another embodiment of the invention a triplex oligonucleotide is provided. The oligonucleotide comprises at least ten nucleotides complementary to a sequence present in a WAF1 gene.

In still another embodiment of the invention a method is provided for promoting growth of cells. The method comprises: administering a WAF1 antisense or triplex-forming oligonucleotide comprising at least ten nucleotides complementary to WAF1 mRNA or WAF1 gene, respectively, to said cells to inhibit the expression of WAF1. In an alternative method an antisense WAF1 construct is administered to said cells to inhibit the expression of WAF1. The construct comprises:

a. a transcriptional promoter;

b. a transcriptional terminator;

c. a DNA segment comprising one or more segments of the WAF1 gene, said gene segment located between said promoter and said terminator, said DNA segment being inverted with respect to said promoter and said terminator, whereby RNA produced by transcription of the DNA segment is complementary to a corresponding segment of WAF1 RNA produced by human cells.

In still another embodiment of the invention a method is provided for assessing susceptibility to cancers. The method comprises testing a tissue selected from the group consisting of blood, chorionic villi, amniotic fluid, and a blastomere of a preimplantation embryo, to determine if DNA in said tissue contains a mutant WAF1 gene.

Thus the subject invention provides the art with useful means for diagnosing and treating cancers in humans and other animals. Moreover, it opens new avenues for the design and screening of additional anti-neoplastic therapeutic agents which operate by means of a new mechanism as detailed below. Conversely, the subject invention provides a new approach for promoting the proliferation of cells when large numbers of such cells are desired.

BRIEF DESCRIPTION OF THE DRAWINGS

FIG. 3 shows CDNA and predicted amino acid sequence of human WAF1. The predicted translation begins at nt 76 and ends at nt 567. The nucleotide sequence of human WAF1 has been deposited with GenBank; accession number VO3106.

FIG. 5A shows partial metaphase chromosomes after FISH with the biotin-labeled genomic WAF1 probe (arrow indicates chromosome 6). FIG. 5B shows identical G-banded metaphase chromosomes as in FIG. 5A, documenting the localization of the fluorescent signal to 6p21.2. FIG. 5C shows an idiogram of chromosome 6 (arrow indicates 6p21.2).

FIGS. 7A and 7B show the sequence of the second exon of mouse WAF1. FIG. 7A shows the predicted amino acid sequence of mouse WAF1 shown above the nt sequence. FIG. 7B shows comparison of the predicted amino acid sequences between human and mouse WAF1. Identical amino acids are indicated by a line between human and mouse amino acids, whereas similar amino acids are indicated by a dot.

FIG. 9A) or the human colon tumor line (SW480; FIG. 9B) were transfected with the pCEP4 vector, or vectors encoding sense WAF1, antisense WAF1, mutant WAF1, or wild-type p53, as indicated. The photographs show low power views of the transfected flasks following 17 days of hygromycin selection. Below each photograph, the fraction of colonies (%) in each flask compared to the vector transfected cells is indicated (means of three flasks±standard deviation). The vector transfectants contained an average of 310 and 850 colonies in rows A and B, respectively.

DETAILED DESCRIPTION OF THE PREFERRED EMBODIMENTS

One of the major goals of tumor biology is to understand the biochemical nature of the pathways leading to growth suppression. For p53, this understanding has recently been enhanced by finding that p53, a nuclear phosphoprotein, binds to DNA in a sequence-specific manner, and activates transcription from such sequences. A variety of experiments has suggested the hypothesis that genes whose expression is activated by p53 are likely to be mediators of p53 action (Pietenpol et al. (1993) *Cell* (submitted)). It is a discovery of the applicants that WAF1 is such a gene. WAF1 gene expression is induced by p53, and this induction is observed in cell lines from human, mouse, and rat. The data indicate that not only are the coding sequence and exon structure of WAF1 conserved, but also its regulation by p53. This is consistent with the fact that p53 tumor suppressive function is conserved between rodents and humans.

Figure 11:
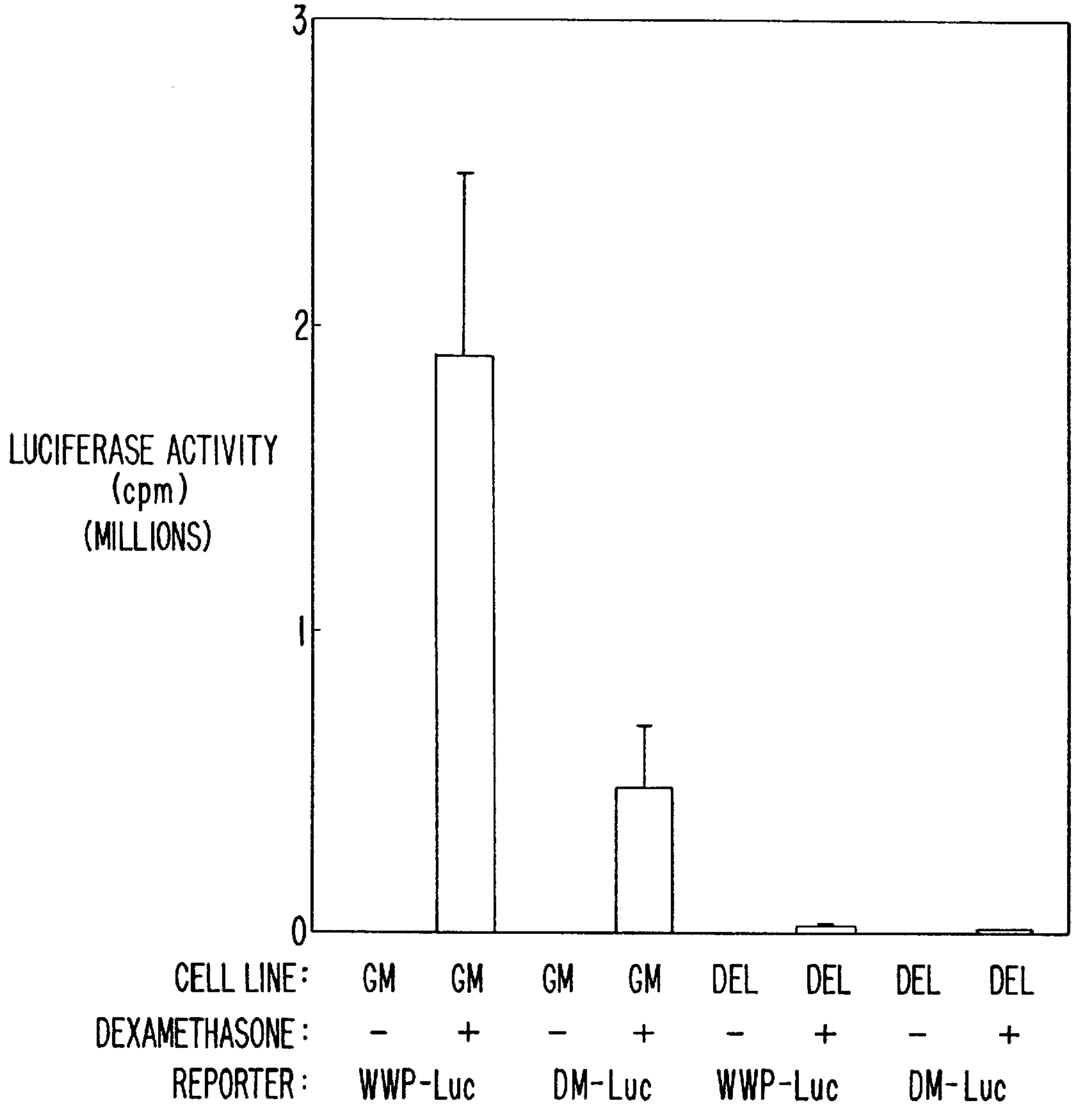
FIG. 11 shows activation of WAF1-promoter by wild-type p53. GM or DEL cells were transfected with either the WWP-Luc or DM-Luc reporters (FIG. 10), and luciferase activity was measured after incubation with or without dexamethasone for 14 hours.

The activation of a gene following wild-type p53 expression could be indirect, a result of induction by a second gene directly controlled by p53. In the case of WAF1, the p53 induction is likely to be direct, as at least one strong binding site exists within its transcription regulatory region. The binding site also functions in a p53-dependent manner in yeast. Moreover, the entire WAF1 promoter region is unambiguously under p53 control in mammalian cells (FIG. 11). Finally, WAF1 mimics the growth suppression of p53 when introduced into three different cell lines. There are a few other genes whose expression is increased as a result of p53 expression, but none of them has been shown to meet the numerous criteria described here for a direct mediator of p53 action.

DNA molecules according to the present invention are isolated and purified from other chromosomal genes. They may be either genomic sequences or cDNA sequences, i.e., they may or may not contain intervening sequences. A genomic clone of about 90 kb has been isolated which encodes the whole WAF1 gene. The WAF1 mRNA has been found to be approximately 2.1 kb. The WAF1 gene contains three exons of 168, 450 and 1600 bp. The sequence of the exons is shown in SEQ ID NO: 1.

Now provided with the sequence of WAF1, one of ordinary skill in the art can readily obtain the 18.1 kd WAF1 protein. It can be expressed in bacteria, yeast, or other convenient cell. Portions of it can be synthesized and linked to a carrier protein for immunization of laboratory animals to raise antibodies specifically immunoreactive with WAF1 protein. The antibodies can be used to purify the WAF1 protein from natural or recombinant sources. Such antibodies can be polyclonal or monoclonal, as is convenient for the particular application.

As described herein, WAF1 protein has a growth-suppressing effect on tumor cells. Thus its administration to tumor cells may be desirable to effect such growth suppression. Other cells which are involved in proliferative diseases may also be targeted for WAF1-mediated growth suppression. Such proliferative diseases include psoriasis, polyps, warts, and inflammatory diseases. WAF1 protein may be administered in suitable formulations to tumor cells. It may be microinjected, or simply supplied externally to tumor cells. It may be encapsulated, e.g., in liposomes. If WAF1-encoding DNA is administered to the tumor cells then the cells can express their own WAF1 protein for growth suppression. Such DNA can be genomic or cDNA, as described above. Other cells involved in proliferative diseases may be treated similarly.

According to another aspect of the invention WAF1 reporter constructs are provided. They are recombinant DNA molecules which contain a WAF1 transcription regulatory region covalently linked in a cis configuration to a reporter gene. Many suitable reporter genes are known in the art, including, but not limited to β-galactosidase, luciferase, chloramphenicol acetyl transferase, neomycin phosphotransferase. If expression of the reporter gene is increased in the presence of a test compound, then one can assume that the test compound will function similarly to increase expression of WAF1 when it is located downstream from its own transcription regulatory region, as it is in vivo. Since increased expression of WAF1 is shown herein to have a growth suppressing effect on tumor cells, it can be assumed that the test compound which enhances the expression of the reporter construct will similarly have a growth suppressive effect in vivo. The transcription regulatory region of WAF 1 which is sensitive to the presence of wild-type p53 is located within about 2.4 kb of the WAF1 transcriptional start site. The region includes the p53 binding site shown in SEQ ID NO:3. If the reporter construct is in a cell, the cell can be incubated with the test compounds and the effect on the expression of the reporter gene can be monitored and measured. Alternatively, the reporter construct may be employed in vitro in cell-free transcription and optionally translation systems.

WAF1 is shown herein to be regulated by wild-type but not mutant p53. Therefore, one can use the expression of WAF1 as a marker for the expression of wild-type p53. Diminished WAF1 expression, relative to normal tissues, can indicate cancer, just as diminished wild-type p53 expression or presence of mutated p53 expression can be indicative of cancer. Assays for WAF1 expression can be used in addition to, or in place of, assays for wild-type p53 directly. Tissues which are suitable for comparison purposes to provide a normal control are typically adjacent, morphologically normal tissues. Tests for the presence or amount of WAF1 expression can employ either antibodies specific for WAF1 protein, nucleic acid probes of at least about 10 nucleotides complementary to all or a portion of the sequence of SEQ ID NO: 1, or other tests known in the art. Similarly, DNA of a tumor tissue can be tested to determine whether it contains mutations. WAF1 mutations would be expected to confer a neoplastic phenotype on cells, as do p53 mutations. Mutations can be determined by determining the sequence of the genes in the tissue being tested, and comparing that sequence to that disclosed in SEQ ID NO: 1. Such mutations may arise in the germline or in somatic tissues. If the mutations arise in somatic tissues, then they will not be found in other tissues of the same individual. If the mutations arise in the germline, they will be found in all tissues of the body, and will, like germlme p53 mutations, indicate a susceptibility to cancers. Tissues suitable for testing for germline mutations include blood, chorionic villi, amniotic fluid, and blastomeres if preimplantation fertilized embryos.

Antisense WAF1 constructs contain a transcriptional promoter and a transcriptional terminator (polyadenylylation signal), with a DNA segment between them. The DNA segment comprises one or more segments of the WAF1 gene, but that segment(s) is in an inverted orientation in the construct, compared to the orientation in the human genome. Transcription from the transcriptional promoter of the construct produces an (antisense) RNA molecule which is complementary to WAF1 RNA which is produced from the WAF1 promoter in normal human cells. The promoter used to make the antisense RNA molecule can be an inducible promoter which can be regulated by certain prescribed stimuli. For example, a metallothionein promoter or a hormone responsive promoter can be advantageously used. Other promoters and terminators can be used as is convenient in the particular application.

The antisense WAF1 constructs of the present invention can be used in one type of cell to produce antisense RNA which is then applied to other cells by techniques known in the art. Alternatively, the WAF1 constructs can be administered to the ultimate target cells in which regulation of WAF1 is desired. Suitable means for introducing DNA constructs into cells are known in the art. Administration of antisense constructs may be by transfection, transformation, electroporation, fusion, etc., as is known in the art. Inhibition of WAF1 expression causes cells to proliferate and prevents cell death. This can be particularly useful in situations where growing large numbers of certain cells in culture is desirable, such as in the case of culturing epidermal cells for transplantation. Alternatively, administration to certain cells of the body may be desirable, such as immune cells or cells of the gastrointestinal tract.

WAF1 antisense oligonucleotides are also provided for the same purpose as the antisense constructs, discussed above. The oligonucleotides are at least ten nucleotides and may be twenty or thirty nucleotides in length. They may consist of normal nucleotides or nucleotide analogs or mixtures of the two. Analogs include methylphosphonates, aminoalkylphosphonates, phosphorothioates, phosphorodithioates, substituted or unsubstituted phosphoramidates. The antisense oligonucleotides are typically linear, single-stranded molecules which are complementary to the natural WAF1 mRNA made by human cells, though circular molecules can also be utilized. These can be administered to cells in liposomes, or naked, for uptake by the cells by passive or receptor-mediated transport. It is often desirable that the antisense oligonucleotide be designed to be complementary to the 5' end of the mRNA, in particular to the translation start site. However, other portions of mRNA molecules have been found to be amenable to antisense inhibition, and may be used in the practice of the present invention. It is also desirable to avoid portions of the mRNA as target for the antisense oligonucleotides which have secondary structures which involve hydrogen bonding with other portions of the molecule. For example, it is desirable to avoid regions which appear to be involved in formation of stems of stem-loop structures.

Some suitable oligonucleotide sequences which may be used are: 5'-GGTTCTGACATGGCGCCTCC-3'; 5'-CCCAGCCGGTTCTGACATGG-3'; 5'-ATGCAGCCCGCCATTAGCGC-3'; 5'-GTCATGCTGGTCTGCCGCCG-3'; 5'-GTGGGCGGATTAGGGCTTCC-3'; 5'-TAAATAGTATTTCATAAAAT-3'. These correspond to nucleotides number 67–86, 74–93, 181–200, 499–518, 560–579, 803–822, of the WAF1 cDNA shown in SEQ ID NO: 1.

The expression of WAF1 may also be inhibited by interference with transcription, by adding oligonucleotides or modified oligonucleotides than can form triple-stranded structures (triplexes) by complexing with a segment of the WAF1 gene.

EXAMPLE 1

This example demonstrates an experimental gene expression system which is sensitive to and specific for the presence of wild-type p53.

As a first step towards the isolation of p53-regulated genes, we determined optimal cell culture conditions under which an exogenous wild-type p53 protein could activate transcription through specific DNA binding. A reporter plasmid containing a p53 DNA-binding site upstream of a basal promoter (Kern et al. (1992) *Science* 256, 827–830) linked to a luciferase reporter gene (PG13-Luc) was cloned and cotransfected into SW480 colon cancer cells with either a human wild-type p53 expression plasmid (p53-wt) or a mutant p53 expression plasmid (p53-273). High luciferase activity was observed only when wild-type p53 was present (data not shown). No luciferase activity was detected if the reporter plasmid contained mutant p53 binding sites (MG15-Luc), regardless of whether or not wild-type p53 was present. This validated reporter was then used in a p53-inducible system.

Figure 1:
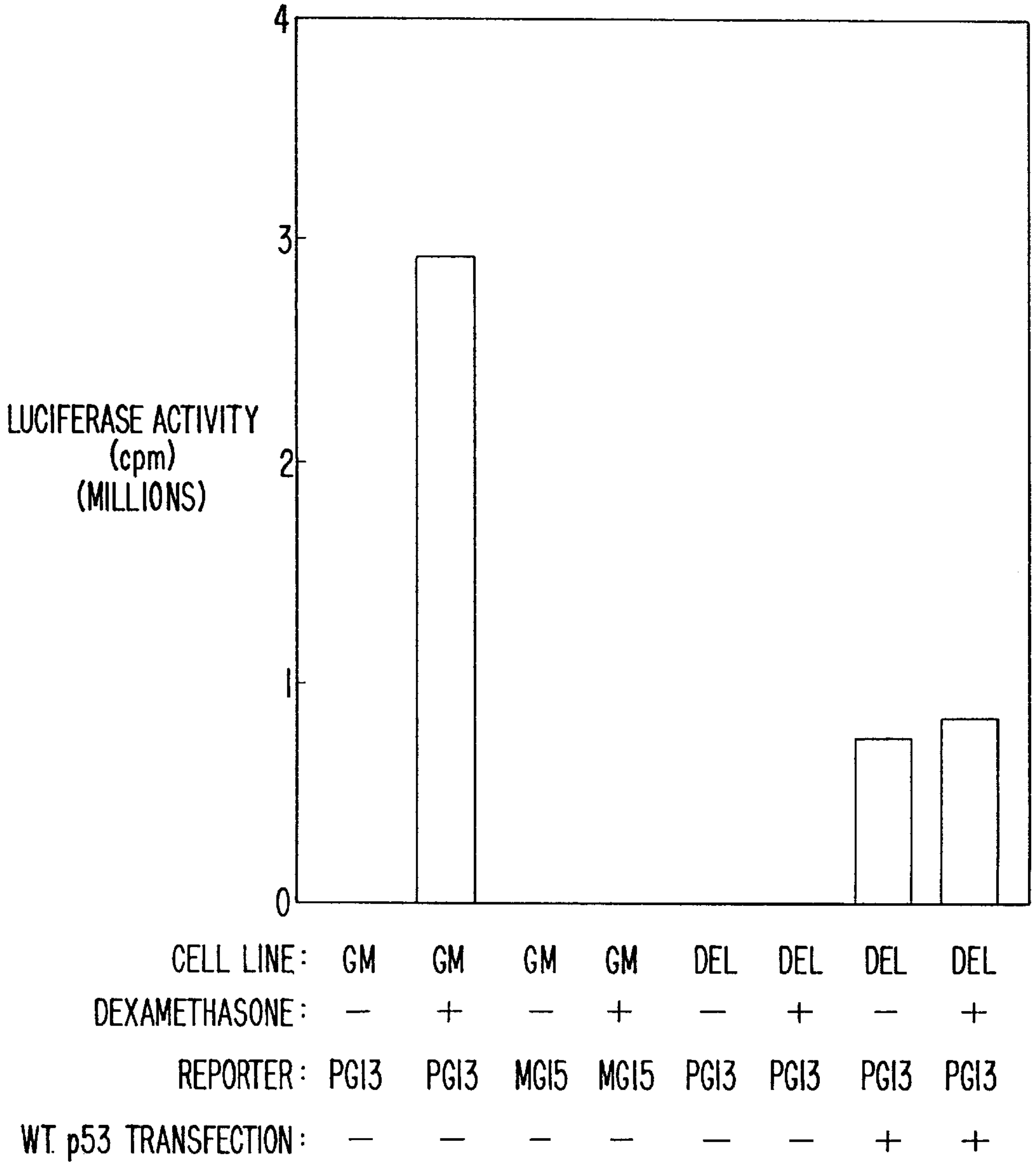
FIG. 1 shows p53-dependent transactivation in GM and DEL cell lines. GM cells (containing an inducible wild-type p53 gene) or DEL cells (containing an inducible mutant p53 gene) were transfected with reporter plasmids as indicated, and luciferase activity was measured after 18 hours of incubation either in the absence or presence of dexamethasone as shown. Wild-type p53 expression plasmid was co-transfected with PG13-Luc into DEL cells as indicated in the two right-most lanes.

The glioblastoma cell line GM contains endogenous mutant p53 (Ullrich et al. (1992) *Oncogene* 7, 1635–1643) and dexamethasone-inducible exogenous human wild-type p53 (Mercer et al. (1990) *Proc. Natl. Acad. Sci. USA* 87, 6166–6170). The related line DEL expresses the same endogenous mutant p53 and a dexamethasone-inducible exogenous mutant p53 (Lin et al. (1992) *Natl. Acad. Sci. USA* 89, 9210–9214). Both cell lines were transfected with either PG13-Luc or MG15-Luc and incubated in the presence or absence of dexamethasone. FIG. 1 shows that dexamethasone-induced wild-type p53 (GM) but not mutant p53 (DEL) expression activated transcription of the luciferase reporter gene linked to a p53 binding site. No luciferase activity was observed when the p53 binding site was mutant (MG15-Luc), or when the p53 protein was mutant (GM without dexamethasone or DEL with or without dexamethasone). Transfection of wild-type p53 into DEL cells activated the PG13-Luc reporter with or without dexamethasone (FIG. 1), confirming that the failure of expression of luciferase reporter gene in this cell line was due to the absence of wild-type p53. These experiments demonstrated that reporter gene expression in these two cell lines was both sensitive and specific to the presence of wild-type p53.

Methods

The SW480 colon cancer cell line was maintained in culture as previously described (Baker et al. (1990) *Science* 249, 912–915). GM4723 (GM cells) and del4A (DEL cells) lines were passaged in Eagle's minimal essential media and log phase cells were induced with dexamethasone as previously described (Mercer et al. (1990) *Proc. Natl. Acad. Sci. USA* 87, 6166–6170). PG13-Luc and MG15-Luc plasmids were cloned by inserting the Hind III/EcoR I fragments containing wild-type or mutant p53 binding elements (PG13-CAT and MG15-CAT; Kern et al. (1992) *Science* 256, 827–830) into the Hind III/EcoRI sites of pBluescript II SK+ (pBS; Stratagene, La Jolla, Calif.). PG13 contains 13 copies of a p53 binding site, while MG15 contains 15 copies of a subtly mutated p53 binding site. The 200 bp EcoR I/BamH I fragment containing the polyoma promoter (from pBEL.Py; Munholland et al. (1992) *EMBO J.* 11, 177–184) was cloned into pBS constructs containing either PG13 or MG15. A 2.6 kb Sac I luciferase cassette (or a 3 kb beta-galactosidase cassette, see below) without promoter elements, was then cloned downstream to create either PG13-Luc or MG15-Luc.

Transfected cells were washed twice with 4 ml Dulbecco's PBS per T-25 flask. The cells were lysed with 0.3 ml (per T-25) of 1×CCLR buffer (Promega, Madison, Wis.) for 10 minutes at room temperature. After a 5 second spin to pellet large debris, 10 μl of supernatant was added to 90 μl of reconstituted Luciferase Assay Reagent (Promega). Light emission was detected by scintillation counting.

EXAMPLE 2

This example demonstrates the isolation of a wild-type p53 activated fragment (WAF1) by subtractive hybridization.

Figure 2:
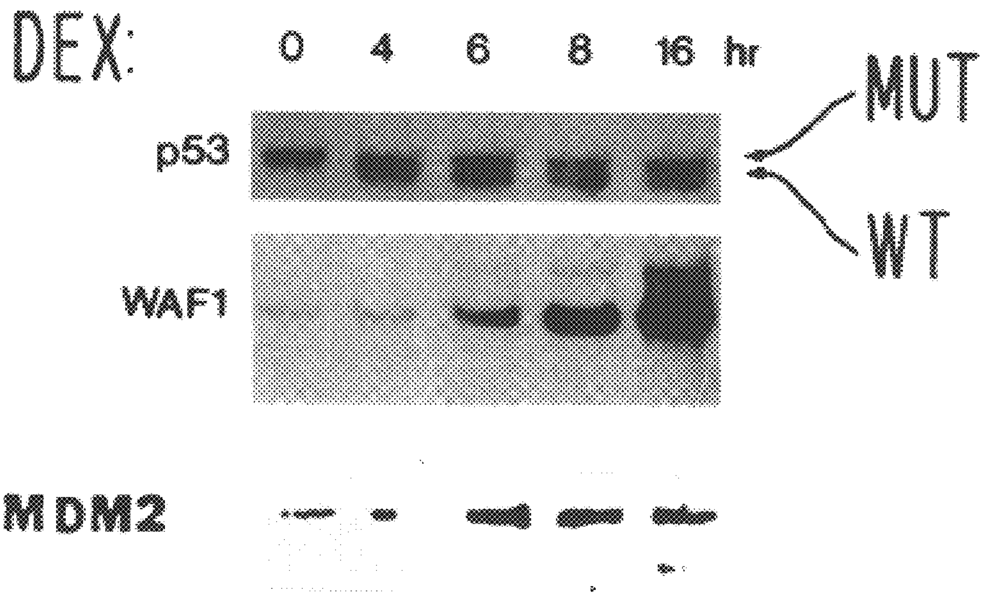
FIG. 2 shows the time course of induction of p53, WAF1, and MDM2 transcripts in GM cells treated with dexamethasone. A Northern blot was prepared using 10 $\mu$g of total RNA isolated from GM cells treated with dexamethasone for 0, 4, 6, 8, or 16 hours, and probed with p53 cDNA (top panel), WAF1 cDNA (middle panel), or MDM2 cDNA (lower panel). The endogenous mutant (mut) and induced wild-type (wt) p53 mRNA species are indicated with arrows.

Based on the reporter gene experiments, we chose to use subtractive hybridization to identify endogenous genes regulated by p53 in GM cells. In order to determine the optimal time to isolate RNA enriched for p53-induced genes, Northern blot analysis was performed, using RNA isolated from GM cells at various intervals following dexamethasone induction. FIG. 2 shows that under the logarithmic growth conditions used, the exogenous wild-type p53 mRNA was detectable by 4 hours after induction and remained elevated for at least 16 hours in GM cells upon dexamethasone induction. A p53-induced cDNA library was therefore prepared from GM cells treated with dexamethasone for 6 hours.

Eighty percent of the clones obtained carried inserts, generally of 1.5- to 2.0-kb in length. A total of 120,000 clones were screened by hybridization to a subtracted p53-induced cDNA probe. This probe was made from cDNA of dexamethasone-induced GM cells after subtraction with an excess of dexamethasone-induced DEL RNA. Control experiments showed that the subtraction procedure used, involving chemical crosslinking (Hampson et al. (1992) *Nucl. Acids Res.* 20, 2899) provided an enrichment of over 100-fold for cDNA sequences not present in the RNA used for subtraction (data not shown). Following hybridization to the subtracted probe, the clones were rehybridized to a probe made from RNA of dexamethasone-induced DEL cells. A total of 99 clones differentially hybridized to the subtracted probe on the initial screen and forty-five of these reproducibly displayed differential hybridization when re-tested.

Hybridization probes were prepared from these clones and used in Northern blots containing RNA isolated from dexamethasone treated or untreated GM cells. Of the 45 clones, 28 were found to be highly induced upon dexamethasone treatment. The other 27 clones were less induced by dexamethasone, and were not studied further. Hybridization, sequencing and restriction endonuclease analysis indicated that all of the 28 highly induced cDNA clones were derived from a single 2.1 kb mRNA. The gene encoding this message was named WAF1 (wild-type p53 activated fragment #1). Rehybridization to the cDNA library revealed that WAF1 cDNA was present at a frequency of 0.4% following dexamethasone induction.

Methods 3.5 μg poly A+ RNA obtained from GM cells induced with dexamethasone for 6 hours was isolated using oligo-dT cellulose (Clontech, Palo Alto, Calif.) according to the supplier's recommendations, from total RNA prepared by CsCl gradient ultracentrifugation of guanidine isothiocyanate lysed cells, as described (Davis, L. G., et. al. (1986) Elsevier Science Pub. Co., Inc.). The poly A+ RNA was used to make an oligo-dT primed cDNA library with the SuperScript Choice System (BRL Research Products Life Technologies, Grand Island, N.Y.). A total of 100 ng of cDNA, comprising the 1.5 to 5 kb fraction, was ligated to lambda Ziplox EcoR I arms (Gibco BRL Life Technologies, Inc., Gaithersburg, Md.), and phage clones were obtained following infection of *E. coli* strain Y109OZL. Phage clones were screened by hybridization of colony lifts to either subtracted or unsubtracted cDNA probes prepared as described below. Excision of pZLI plasmid clones was carried out by phage infection of the excision strain DH1OB-Zip (Elledge et al. (1991) *Proc. Natl. Acad. Sci. USA* 88, 1731–1735).

Unsubtracted cDNA probes were prepared from 2 μg poly A+ RNA "driver" using oligo-dT as primer and MMLV Super-Script II as described (Hampson et al., (1992) *Nucl. Acids Res.* 20, 2899), except that following alkaline hydrolysis with NaOH and neutralization with HCl, the cDNA was isopropanol precipitated in the presence of 0.17 M sodium perchlorate, washed with 70% ethanol, vacuum dried and resuspended in 10 μl of water (Kinzler et al. (1989) *Nucl. Acids Res.* 17, 3645–3653). Twenty ng of unsubtracted cDNA was then labelled with random primers using Sequenase as described (Hampson et al. (1992) *Nucl. Acids Res.* 20, 2899). Subtracted cDNA probes were prepared after a 22 hour hybridization of 500 ng "target" cDNA to 10 μg poly A+ "driver" RNA, chemical crosslinking with 2,5-diaziridinyl-1,4-benzoquinone (generously provided by John Butler), and labelling as described (Hampson et al. (1992) *Nucl. Acids Res.* 20, 2899).

EXAMPLE 3

This example demonstrates the structure of the WAF1 gene.

Figure 4:
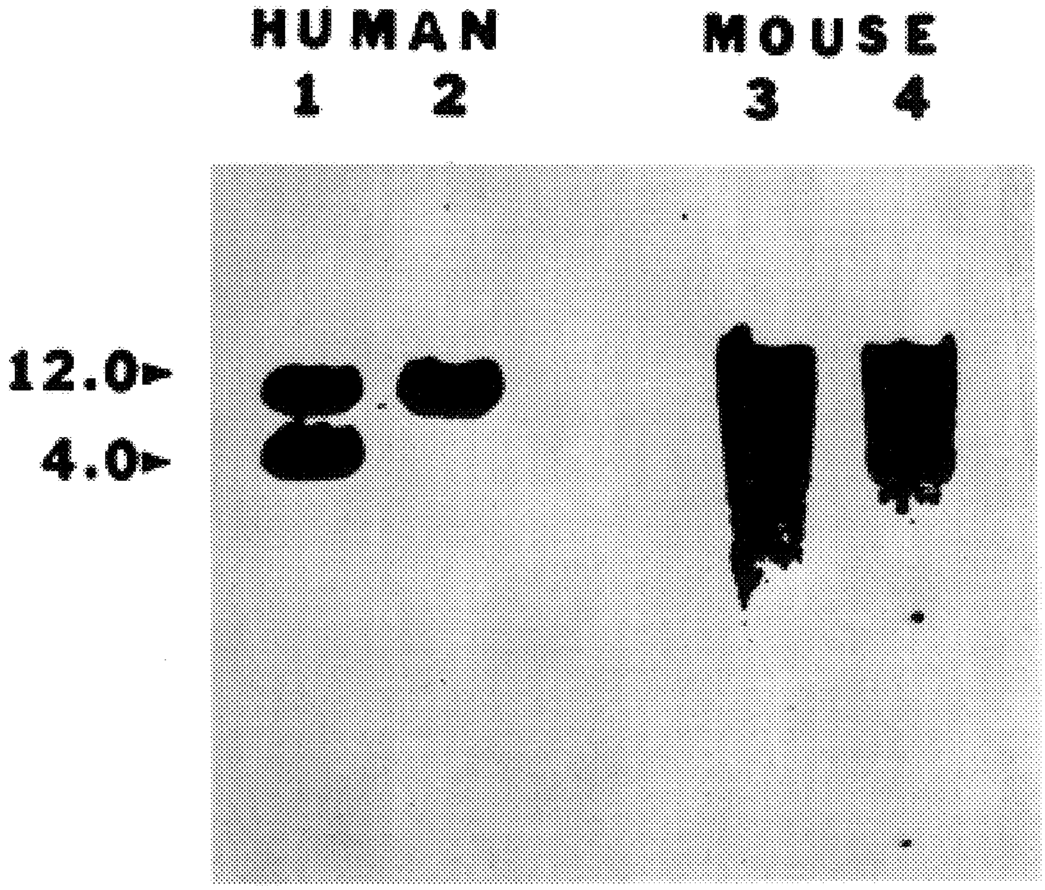
FIG. 4 shows Southern blot analysis of WAF1 in human and mouse cells. Four $\mu$g of human genomic DNA (lanes 1 and 2) or 8 $\mu$g of mouse genomic DNA (lanes 3 and 4) were digested with EcoRI (lanes 1 and 3) or BamHI (lanes 2 and 4). Following transfer, the blot was probed with a radioactively labeled WAF1 cDNA fragment encompassing WAF1 nt 1 to 1004.

Eighteen of the 28 WAF1 clones appeared to contain near full-length cDNA, predicted to be 2.1 kb on the basis of Northern blot analysis (FIG. 2). DNA sequencing revealed that most of the clones contained the same 5'-end. Because the cDNA library used was not amplified, this likely represented the 5'-end of the transcript. The WAF1 cDNA sequence is shown in FIG. 3. (SEQ ID NO: 1) The first ATG codon occurred at nucleotide 77, and an in-frame termination codon occurred at nucleotide 570, predicting a translation product of 18.1 kd. In vitro transcription and translation of WAF1 cDNA clones produced a protein of the expected size (not shown). Analysis of the amino-acid sequence of WAF1 protein revealed a cysteine-rich region $C(X)_4C(X)_{15}$, $C(X)_6C$ between amino acids 13 and 41 with the potential for zinc-binding (Berg, *Science* 232:485–487 (1986)), and a basic region between amino acids 140 and 163 containing two potential bipartite nuclear localization signals (Robbins et al., *Cell* 64:615–623 (1991)) near the C-terminus (SEQ ID NO: 2) No significant homologies at the amino-acid level were found to known proteins (NBRF-PIR release #35.0). Southern blot analysis showed that WAF1 was probably a single copy gene, with no close relatives in the human genome (FIG. 4).

Methods

Northern blot analysis was performed as previously described (El-Deiry et al. (1991) *Proc. Natl. Acad. Sci. USA* 88, 3470–3474) except that Quickhyb (Stratagene, La Jolla, Calif.) was used as the hybridization solution.

EXAMPLE 4

This example demonstrates that WAF1 is localized to chromosome 6, band p21.2 of the human genome.

Figure 5A:
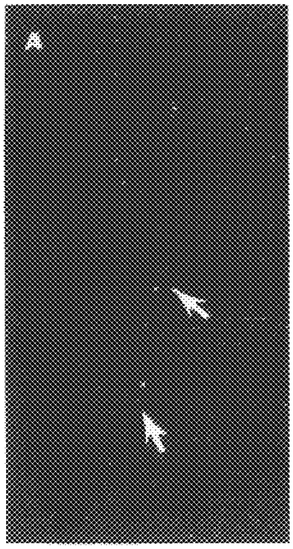
FIGS. 5A–5C show chromosomal localization of the gene encoding WAF1.
Figure 5B:
Figure 5C:
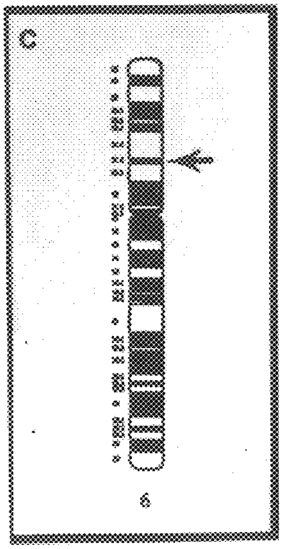

To identify the chromosomal location of the WAF1 gene, a human genomic P1 clone (P1-WAF1) containing WAF1 sequences was obtained (as described below). The clone contained about 90 kb of DNA, and partial sequencing revealed that the WAF1 gene consisted of three exons of 68, 450, and 1600 bp (exons 1, 2, and 3 respectively). The translation initiation signal was contained in exon 2, a relatively long coding exon (Sterner et al (1993) *Mol. and Cell. Biol.* 13, 2677–2687). The P1-WAF1 clone was labelled with biotin and hybridized to metaphase chromosomes as previously described (Meltzer et al. (1992) *Nature Genet.* 1, 24–28). A total of 18 metaphase cells were examined, and each had at least one "double" fluorescent signal (i.e., signals on each of 2 chromatids) on the middle of the short arm of chromosome 6 (FIG. 5). In 15/18 cells, double signals were observed on both chromosome 6 homologs. Only chromosomes in which both chromatids displayed a signal were included for analysis, making the background hybridization close to zero. The same cells subjected to FISH had been previously G-banded using Trypsin-Giemsa and photographed to allow direct comparison of the results. The results demonstrated that sequences hybridizing to WAF1 DNA fragment were localized to 6p21.2.

Methods

A screen of human genomic P1 clones for WAF1 was performed using the primers 5'-CTTTCTAGGAGGGAGACAC-3' (SEQ ID NO:1) and 5'-GTTCCGCTGCTAATCAAAG-3' (SEQ ID NO:1) from WAF1 exon 3 for PCR (Genome Systems, Inc., St. Louis, Mo.). The PCR was performed using the Bind-Aid kit (USB) in a 25 μl reaction containing 2.5 μl 10× USB PCR buffer, 2 μl 2.5 mM each dNTP (dATP, dCTP, dGTP, and dTTP), 0.5 μl Bind-Aid (0.5 μg/μl SSB), 0.5 μl each primer (350 ng/μl), 10 ng DNA template, and 2 Units AmpliTaq (Perkin Elmer Cetus). Amplification was carried out for 35 cycles (following the profile: 95° C. for 30 seconds, 57.5° C. for 1 minute, and 70° C. for 1 minute), yielding a 99 bp PCR product. The P1 clone obtained (P1-WAF1) was labelled with biotin and hybridized to metaphase chromosomes as previously described (Meltzer et al. (1992) *Nature Genet.* 1, 24–28). Eighteen metaphase nuclei were examined for WAF1 localization.

EXAMPLE 5

This example demonstrates that (1) WAF1 is induced in more than one cell type following wild-type p53 expression; (ii) WAF1 is highly conserved among species; and (iii) WAF1 is induced by p53 in other species.

Figure 6:
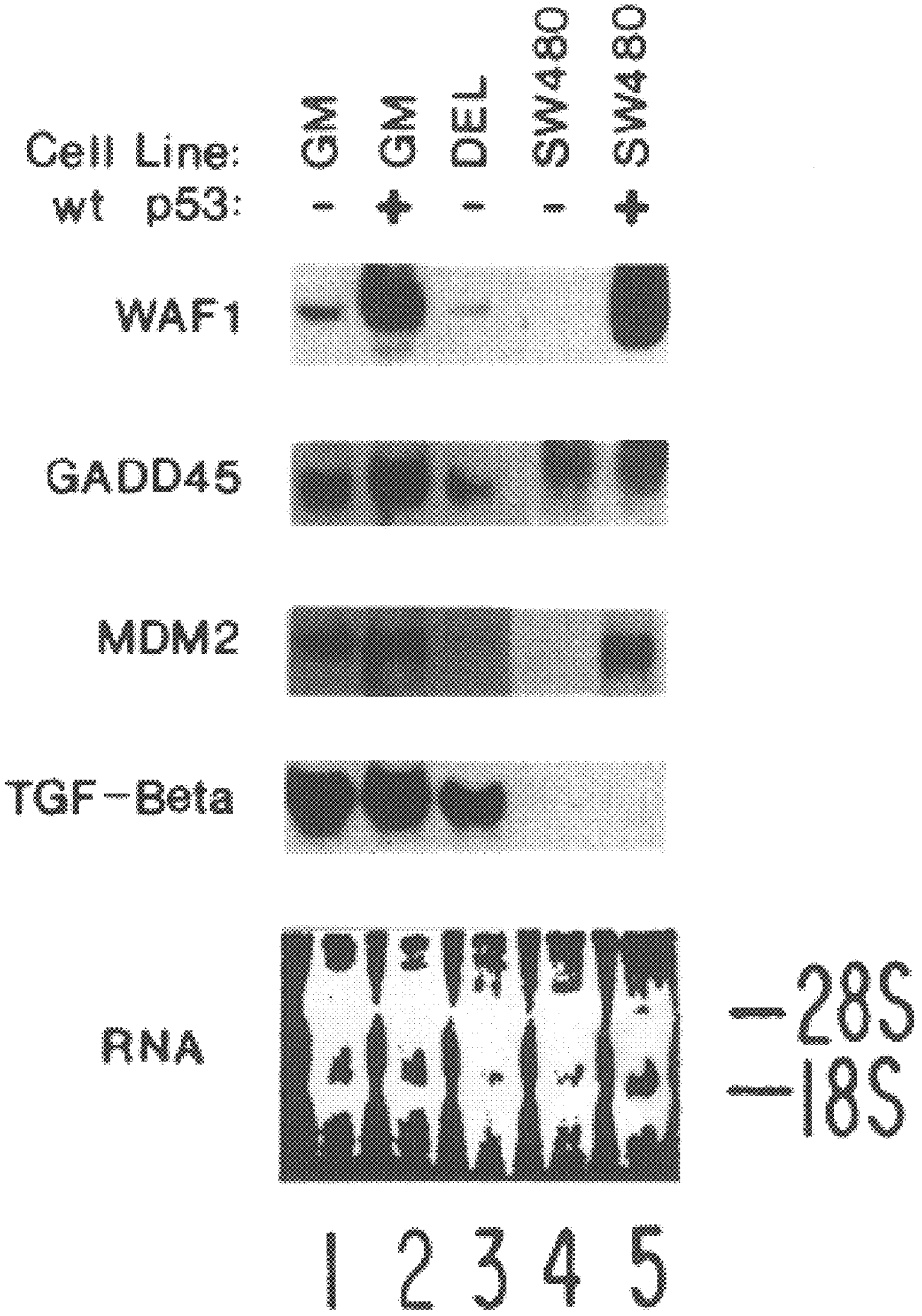
FIG. 6 shows that WAF1 is induced in the presence of transcriptionally active wild-type p53. A Northern blot was prepared from 10 μg of total RNA from GM cells in the presence or absence of dexamethasone for 16 hours (lanes 1 and 2 respectively), DEL cells treated with dexamethasone (lane 3), or SW480 cells infected with either Ad-gal (lane 4) or Ad-p53 (lane 5) for 16 hours. The blot was probed with WAF1 DNA, GADD45 DNA, MDM2 DNA, or TGF-beta DNA, as indicated. An ethidium bromide stain of the RNA, prior to Northern transfer, is shown in the lower-most panel. The expression of wild-type p53 in the various cells is indicated at the top of the figure.

FIG. 6 illustrates the expression of WAF1 in GM cells following dexamethasone treatment for 16 hours (lane 2), compared to either uninduced GM cells (lane 1) or dexamethasone treated DEL cells containing induced mutant p53 (lane 3). Controls for the experiment included two other genes known to be induced by p53, MDM2 and GADD45, as well as an unrelated gene, TGF-beta. Both MDM2 and GADD45 were induced in the GM cells when wild-type p53 was present, but much less so than WAF1.

To examine the induction of WAF1 by wild-type p53 in a different cell line, a wild-type p53 construct in an adenoviral vector (Ad-p53) was used to infect human SW490 colon cancer cells. That Ad-p53 produced transcriptionally active p53 was demonstrated by assaying an SW480 cell line carrying a stably integrated reporter responsive to wild-type but not mutant p53 as described below. SW480 cells were infected with either Ad-p53 or Ad-gal (a control adenoviral vector producing beta-galactosidase instead of p53) for 16 hours and RNA used for Northern blot analysis. FIG. 6 shows that WAF1 was highly induced in SW480 cells infected with Ad-p53 (lane 5), but not those infected with Ad-gal (lane 4).

We next assessed the evolutionary conservation of WAF1. "Zoo blots" revealed that single copy sequences from mouse cells hybridized to the human WAF1 clone (FIG. 4). Attempts to clone a mouse WAF1 cDNA from a mouse adult brain cDNA library were unsuccessful. Therefore, we obtained a mouse genomic clone containing the WAF1 gene as described below. The nucleotide and predicted amino acid sequence of the mouse WAF1 (mWAF1) second exon is shown in FIG. 7A. The mouse and human WAF1 second exon sequences were 76% identical and 80% similar at the amino acid level (FIG. 7B). A stretch of 26 amino acids (human aa 21–56) was almost perfectly conserved, as was the zinc finger-like motif between aa 13 and 41 in human WAF1 ($H(X)_4C(X)_{15}C(X)_6C$ in the mouse). The positions of introns surrounding exon 2 in the WAF1 gene were identical in both human and mouse (not shown).

Figure 8:
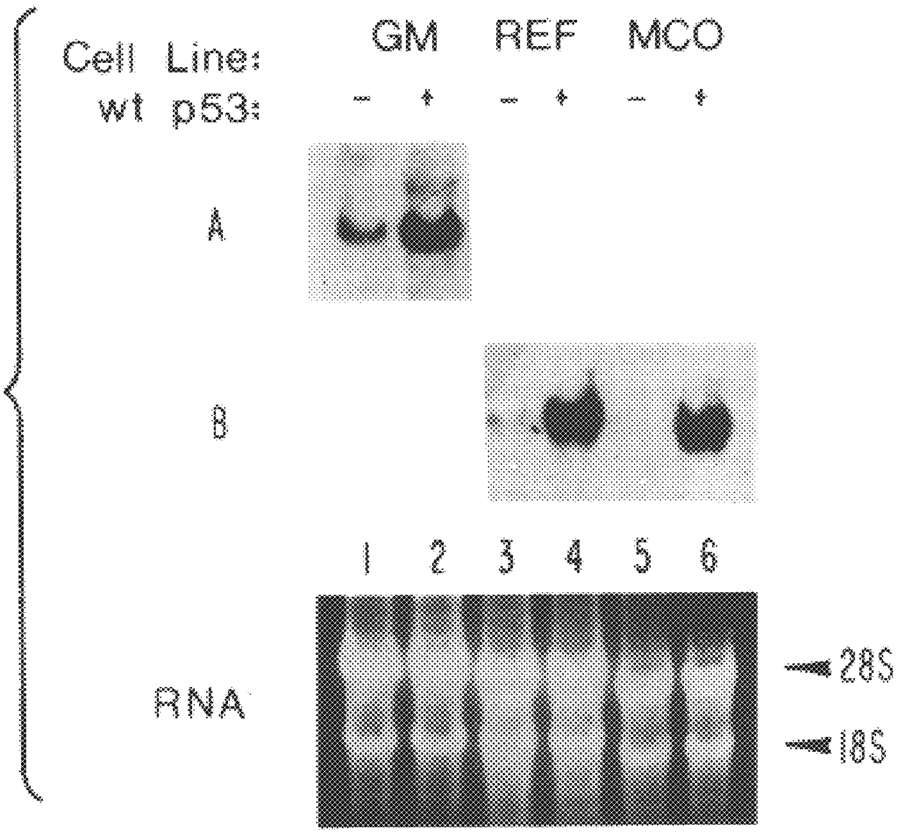
FIG. 8 shows that WAF1 induction by p53 is conserved in rat and mouse. A Northern blot was prepared using total RNA from GM cells, either untreated (lane 1) or treated for 6 hours with dexamethasone (lane 2), REF 112 cells grown either at 37° C. (uninduced; lane 3) or 31° C. (lane 4), or MCO1 cells infected with either Ad-gal (lane 5) or Ad-p53 (lane 6). The RNA was hybridized with radioactive probes made from human WAF1 cDNA (FIG. 7A) or mouse WAF1 DNA (FIG. 7B). An ethidium bromide stain of the RNA, prior to transfer, is shown in the lowest panel.

To determine whether rodent WAF1 gene expression was induced by wild-type p53, two experimental systems were used. The first consisted of rat embryo fibroblasts containing a stably integrated murine temperature-sensitive mutant p53 (REF-112 cells; Michalovitz et al. (1990) *Cell* 62, 671–680). These cells were transfected with the PG13-Luc reporter and incubated either at 37° C. (mutant p53 conformation), or 31° C. (wild-type p53 conformation) for 24 hours. No measurable increase in luciferase activity was observed at 37° C., but luciferase activity increased 1000-fold at 31° C., confirming the presence of transcriptionally active murine wild-type p53 at the latter temperature. RNA was then prepared from REF-112 cells incubated for 14 hours either at 37° C. or 31° C. FIG. 8 shows that expression of WAF1 mRNA was detected at 31° C. but not at 37° C., demonstrating that the WAF1 gene is conserved in rat, and that the gene is inducible by the murine p53 at the wild-type permissive temperature.

Second, the murine fibrosarcoma cell line MCO1 (Halevy et al. (1991) *Oncogene* 6, 1593–1600), which lacks p53 due to a splice site mutation and a deletion, was infected with either Ad-p53 or Ad-gal. At 22-hours following adenoviral infection, RNA was prepared and used in Northern blot analysis. FIG. 8 shows that mWAF1 was highly induced in MCO1 cells infected with Ad-p53, but not in cells infected with Ad-gal. Thus, WAF1 induction by p53 was conserved in both rat and mouse cells.

The fact that WAF1 was (i) induced in more than one human cell type following wild-type p53 expression; (ii) highly conserved among species; and (iii) induced by p53 in other species, suggests that WAF1 is important for p53 function.

Methods

The MDM2 probe was made from a 1.6 kb cDNA fragment (Oliner, J. D. et al. (1993) *Nature* 362, 857–860), and the GADD45 probe was generously provided by A. Fornace (Kastan et al. (1992) *Cell* 71, 587–597). Probes were made by oligo-labelling DNA fragments isolated from agarose gels (Feinberg, A. P. and Vogelstein, B. (1983) *Anal. Biochem.* 132, 6–13).

A mouse WAF1 (mWAF1) genomic clone was isolated by screening $1\times10^6$ clones of a mouse genomic DNA library in Lambda Fix II (Stratagene), using the human WAF1 cDNA as a probe. One hybridizing clone was obtained. An 11 kb Hind III fragment containing the second exon of mWAF1 was subcloned into the Hind III site of pBS. An 0.3 kb Pst I fragment from this clone (containing part of mWAF1 exon 2) was used to probe the Northern blot in FIG. 8.

The cDNA for p53 was obtained as a BamH I fragment from the p53-wt vector (Baker et al. (1990) *Science* 249, 912–915; Kern et al. (1992) *Science* 256, 827–830) and cloned into the BamH I site of pMV10 (Wilkinson, G. W. G., and Akrigg, A. (1992) *Nucl. Acids Res.* 20, 2233–2239). The Hind III fragment of pMV10-p53-wt was then subcloned into the Hind III site of the pMV60 vector (Wilkinson, G. W. G., and Akrigg, A. (1992) *Nucl. Acids Res.* 20, 2233–2239) to make the vector pMV60-p53-wt. The plasmids pMV60-p53-wt and pJM17 (Wilkinson, G. W. G., and Akrigg, A. (1992) *Nucl. Acids Res.* 20, 2233–2239) were co-transfected into 293 cells. Recombinants were plaque purified and tested for production of transcriptionally active p53 by infection of the SW480-IAB3 cell line. A plaque purified recombinant (Ad-p53) induced beta-galactosidase activity in infected SW480-IAB3 cells. The beta-galactosidase producing defective adenovirus (Ad-gal) was obtained from plaque purified recombinants following co-transfection of 293 cells with pMV35 and pJM17. Both Ad-p53 and Ad-gal were further purified by CsCl banding.

The SW480-IAB3 cell line was obtained following co-transfection of SW480 cells with plasmids PG13-Gal and pCMV-Neo-Bam (Baker et al. (1990) *Science* 249, 912–915), and selection with genetecin. Individual clones were isolated by limiting dilution and tested for the presence of stably integrated intact reporter by transfection with either plasmid p53-wt or p53-143 (Kern et al. (1992) *Science* 256, 827–830) followed 24 hours later by in-situ X-gal staining. The SW480-IAB3 was chosen for passaging because no beta-galactosidase activity was detectable unless wild-type p53 was present in the cells. The cells were maintained in Leibovitz L15 medium supplemented with 10% fetal bovine serum and 0.5 mg/ml genetecin. REF-112 and MCO1 cells were obtained through the generosity of Moshe Oren. For transfection experiments, $1.5\times10^6$ cells were plated in 25-$cm^2$ tissue culture flasks 24 hours before transfection. A total of 5 $\mu$g of CsCl banded DNA and 25 $\mu$g Lipofectin (Bethesda Research Laboratories, Gaithersburg, Md.) were used for transfections. For growth inhibition experiments (FIG. 9), hygromycin (0.25 mg/ml) selection began 24 hours after transfection.

EXAMPLE 6

This example demonstrates that WAF1 suppresses tumor cell growth.

If WAF1 played a role in mediating the tumor growth inhibition of p53, one might expect it to have a growth suppressive role of its own. To address this possibility, mammalian expression vectors containing p53 cDNA or WAF1 cDNA in either the sense (pC-WAF1-S) or antisense (pC-WAF1-AS) orientation were constructed. The vectors each contained a gene conferring hygromycin resistance in addition to the cDNA. The vectors were transfected into SW480 cells, previously shown to be inhibited by wild-type p53 expression (Baker et al. (1990) *Science* 249, 912–915). Following transfection, cells were grown in the presence of hygromycin and the number of colonies was scored after 2–3 weeks.

Figure 9:
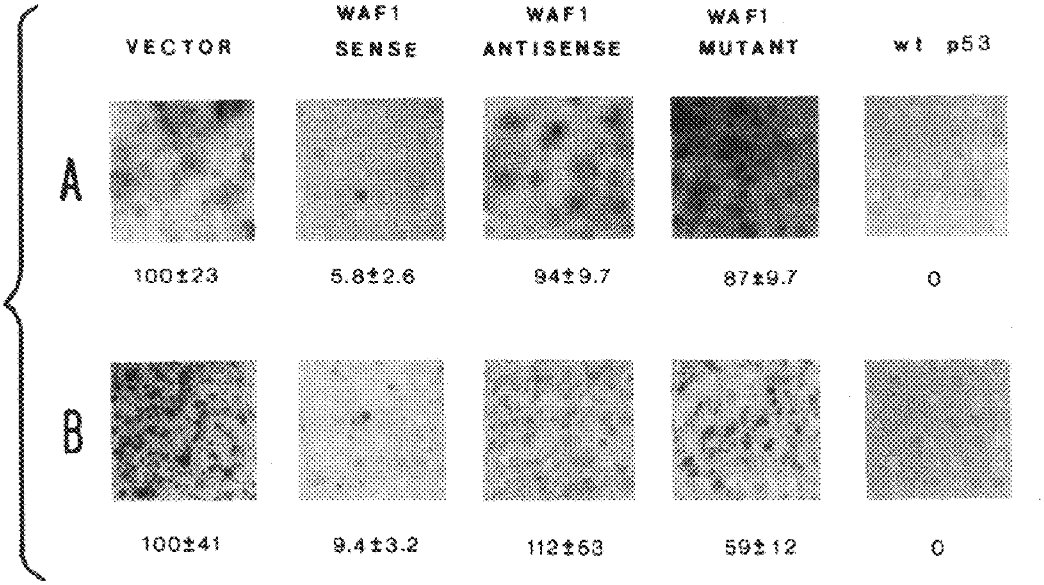
FIGS. 9A and 9B show that WAF1 suppresses the growth of human tumor cells. The human brain tumor line (DEL.

The data in FIG. 9 show that introduction of WAF1 sense cDNA expression vectors resulted in substantial growth suppression, as seen by a 10–20 fold decrease in the number of hygromycin-resistant colonies. This growth suppression was similar to, but not as complete as, that observed with p53 (FIG. 9). Introduction of the WAF1 antisense cDNA expression vector, or the vector devoid of WAF1 sequences, resulted in a similar number of clones. The few small clones which did appear after transfection of the WAF1 sense cDNA expression vector grew at a slow rate and could not be passaged. Similar results were obtained in four separate experiments, each with triplicate transfections, using different preparations of plasmid DNA. We additionally used the brain tumor cell lines GM and DEL in similar experiments, and found that their growth was also suppressed by the introduction of wild-type WAF1 (FIG. 9 and data not shown). As an additional control, we constructed a WAF1 mutant (pC-WAF1-ES), with a stop codon at nt 222. Introduction of pC-WAF1-ES into either SW480 or DEL cells did not result in significant growth suppression (FIG. 9).

Methods pC-WAF1-S (sense) and pC-WAF1-AS (antisense) expression plasmids were prepared by cloning the full-length WAF1 cDNA as a Not I fragment from cDNA library clone #33 into the Not I site of pCEP4 (Invitrogen). The pC-WAF1-ES mutant vector was similarly obtained from a PCR generated cDNA insert, containing a G to A transition at nt 222, resulting in a stop codon instead of Trp at amino acid 49.

EXAMPLE 7

This example demonstrates that p53 activates the WAF1 promoter.

Figure 10:
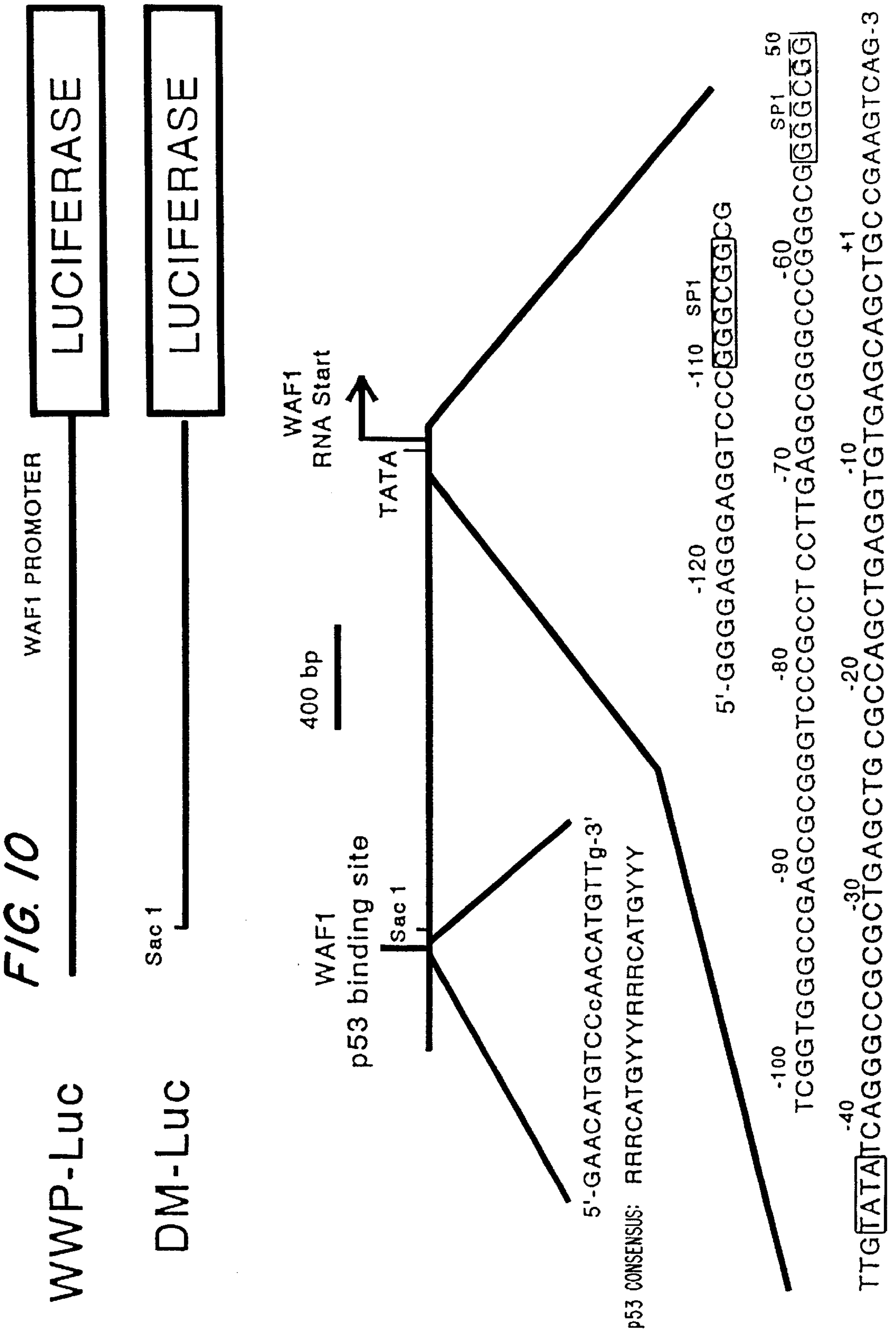
FIG. 10 shows schematic representation of WAF 1 transcription regulatory region. Diagram shows the promoter-reporter constructs (FIG. 10A), and partial DNA sequence of the WAF1 upstream regulatory region (FIG. 10B), including promoter and upstream p53 binding sequences. Small letters in the latter represent deviations from the p53 consensus binding sequence. The TATA-element and Sp1 recognition sequences within the WAF1 promoter are surrounded by boxes. The Sac I site, used for making the DM-Luc construct devoid of the p53 binding site, occurred at the 3'-end of the sequence shown (g is the 1st nt of the Sac I recognition site).

Having demonstrated that WAF1 expression is induced by wild-type p53, we attempted to determine whether this resulted from a direct interaction of p53 with regulatory elements in WAF1. To search for sequences transcriptionally responsive to p53, we used the 90 kb genomic clone P1-WAF1 in a yeast enhancer trap system. In this system, yeast cells auxotrophic for histidine were transformed with a plasmid library constructed by insertion of random fragments of P1-WAF1 upstream of a truncated GAL1 promoter regulating histidine reporter gene expression. Clones were selected for histidine prototropy in the presence of human p53 expression. Three libraries were constructed, using Alu I, Hae III, or Sau 3AI fragments of P1-WAF1. Through the screening of $1.6\times10^{5}$ transformants, 22 wild-type p53-dependent, histidine prototrophs were obtained. No histidine prototropy was observed if yeast expressed mutant instead of wild-type p53. All but one of the 22 clones were found to contain either of two sequence elements, both matching the previously defined p53 binding site consensus. Mapping of the two elements revealed that one of them was located 2.4 kb upstream of WAF1 coding sequences (FIG. 10). Thus, a p53-binding site was present upstream of WAF1, and this element, when placed in an artificial system with a standard promoter, could stimulate expression of a reporter gene in the presence of wild-type p53.

To determine whether the natural promoter elements of WAF1 could mediate p53-dependent transcriptional activation, a 2.4 kb genomic fragment, with its 3'-end at nt 11 of WAF1 cDNA, was cloned upstream of a promoterless luciferase reporter gene. A partial sequence of the WAF1 promoter, and a map of this clone, is shown in FIG. 10. This promoter was G:C rich and contained a TATA-element 43 nt upstream of the putative transcription start site. Two Sp1 binding sites were located at nt-50 and -104, and there was a sequence weakly matching the p53 binding site consensus at nt-75.

FIG. 11 shows that the WAF 1 promoter construct WWP-Luc activated expression of luciferase only in the presence of wild-type p53. In the absence of wild-type p53 (GM cells without dexamethasone or DEL with or without dexamethasone), expression of this reporter was less than 2% of levels observed in the presence of wild-type p53. When the 2 kb upstream p53 binding site was deleted (DM-Luc), the majority of the luciferase activity was abolished, though the residual activity was still wild-type p53-dependent. This observation suggests the presence of a second (weaker) p53 response element within the WAF1 promoter, perhaps at nt-75 (FIG. 10). The same pattern of reporter activation was observed following co-transfection of WWP-Luc or DM-Luc with the wild-type p53 expression plasmid in SW480 cells. There was a 200-fold increase in luciferase activity with wild-type p53 compared to mutant p53 ($273^{His}$) transfection (data not shown). Similar to the GM cell results, luciferase activity decreased by approximately 80% when the upstream p53 response element was absent (DM-Luc construct, FIG. 11).

Methods The P1-WAF1 clone was digested to completion with Hae III, Alu I, or Sau 3AI, subcloned into the plasmid pBM947 and used to identify p53 binding sites by genetic selection in yeast (Wilson et al. (1991) *Science* 252, 1296–1300; T. Tokino et al., unpublished data). A total of 530,000 clones were obtained in *E. coli*, and the DNA from these clones was used to transfect *S. cerevisiae* cells containing a p53 expression vector and a HIS3 gene under the control of p53 binding sequences (Nigro et al. (1992) *Mol. Cell. Biol.* 12, 1357–1365; Kern et al. (1992) *Science* 256, 827–830; T. Tolino and S. Thiagalingam, unpublished data). A total of 160,000 yeast clones were assayed for histidine prototropy. Selection in the absence of histidine allowed the isolation of clones containing a p53 binding sequence; transcriptional activation by p53 resulted in HIS3 production and subsequent survival of the yeast transformants. DNA was isolated from such clones and tested for induction of histidine prototropy in yeast strains with or without human p53 expression vectors.

WWP-Luc and DM-Luc plasmids were cloned by inserting the 2.6 kb BamH I luciferase cassette (from PG13-Luc) into the Xho I sites of pWWP and pDM. The 2.4 kb WAF1 promoter region was obtained as a Hind III cassette by PCR amplifications using a P1-WAF1 subclone as template and the primers 5'-CCACAAGCTTCTGACTTCGGCAG-3' (SEQ ID NO:5) and 5'-CCCAGGAACAAGCTTGGGCAGCAG-3' (SEQ ID NO:6). This cassette was cloned into the Hind III site of pBC KS+ (Stratagene) to yield plasmid pWWP containing the endogenous WAF1 promoter including the upstream p53 binding element near one end and WAF1 nt 11 at the other end (FIG. 10). The plasmid pDM, which lacks the p53 binding element 2.4 kb upstream of WAF1, was obtained by digesting pWWP with Sac I, and recloning the deleted fragment after circularization.

What is claimed is:

1. A method for diagnosing cancer, comprising the steps of:

testing a tissue to determine if the tissue expresses less WAF1 mRNA having a ribonucleotide sequence corresponding to the deoxyribonucleotide sequence as shown in SEQ ID NO: 1 or WAF1 protein having a sequence as shown in SEQ ID NO:2 than normal tissue.

2. The method of claim 1 wherein the step of testing utilizes an antibody which is specifically reactive with WAF1 protein as shown in SEQ ID NO:2.

3. The method of claim 1 wherein the step of testing utilizes a nucleic acid probe which specifically hybridizes to a WAF1 mRNA having a ribonucleotide sequence corresponding to the deoxyribonucleotide sequence as shown in SEQ ID NO:1, said probe having a sequence selected from SEQ ID NO: 1.

4. A method for diagnosing cancer, comprising the steps of:

testing a sample tissue to determine if DNA in said sample tissue contains a mutant WAF1 gene as compared to a wild-type WAF1 gene comprising a sequence as shown in SEQ ID NO: 1.

5. The method of claim 4 wherein DNA of the sample tissue is compared to DNA of a normal tissue to determine whether the WAF1 gene in the sample tissue is mutant.

6. A method for assessing susceptibility to cancers, comprising the step of:

testing a tissue selected from the group consisting of blood, chorionic villi, amniotic fluid, and a blastomere of a preimplantation embryo, to determine if DNA in said tissue contains a mutant WAF1 gene as compared to a wild-type WAF1 gene which comprises a sequence as shown in SEQ ID NO:1.

* * * * *

SEQUENCE LISTING

```
(1) GENERAL INFORMATION:

   (iii) NUMBER OF SEQUENCES: 6


(2) INFORMATION FOR SEQ ID NO:1:

     (i) SEQUENCE CHARACTERISTICS:
          (A) LENGTH: 2121 base pairs
          (B) TYPE: nucleic acid
          (C) STRANDEDNESS: double
          (D) TOPOLOGY: linear
```

-continued (ii) MOLECULE TYPE: cDNA (iii) HYPOTHETICAL: NO (iv) ANTI-SENSE: NO (vi) ORIGINAL SOURCE:
(A) ORGANISM: Homo sapiens
(H) CELL LINE: GM (viii) POSITION IN GENOME:
(A) CHROMOSOME/SEGMENT: 6p21.2

(ix) FEATURE:
(A) NAME/KEY: CDS
(B) LOCATION: 76..568
(D) OTHER INFORMATION: /gene= "WAF1"

(xi) SEQUENCE DESCRIPTION: SEQ ID NO:1:

```
GCCGAAGTCA GTTCCTTGTG GAGCCGGAGC TGGGCGCGGA TTCGCCGAGG CACCGAGGCA     60

CTCAGAGGAG GCGCC ATG TCA GAA CCG GCT GGG GAT GTC CGT CAG AAC CCA     111
                 Met Ser Glu Pro Ala Gly Asp Val Arg Gln Asn Pro
                   1               5                  10

TGC GGC AGC AAG GCC TGC CGC CGC CTC TTC GGC CCA GTG GAC AGC GAG     159
Cys Gly Ser Lys Ala Cys Arg Arg Leu Phe Gly Pro Val Asp Ser Glu
         15                  20                  25

CAG CTG AGC CGC GAC TGT GAT GCG CTA ATG GCG GGC TGC ATC CAG GAG     207
Gln Leu Ser Arg Asp Cys Asp Ala Leu Met Ala Gly Cys Ile Gln Glu
     30                  35                  40

GCC CGT GAG CGA TGG AAC TTC GAC TTT GTC ACC GAG ACA CCA CTG GAG     255
Ala Arg Glu Arg Trp Asn Phe Asp Phe Val Thr Glu Thr Pro Leu Glu
 45                  50                  55                  60

GGT GAC TTC GCC TGG GAG CGT GTG CGG GGC CTT GGC CTG CCC AAG CTC     303
Gly Asp Phe Ala Trp Glu Arg Val Arg Gly Leu Gly Leu Pro Lys Leu
                 65                  70                  75

TAC CTT CCC ACG GGG CCC CGG CGA GGC CGG GAT GAG TTG GGA GGA GGC     351
Tyr Leu Pro Thr Gly Pro Arg Arg Gly Arg Asp Glu Leu Gly Gly Gly
             80                  85                  90

AGG CGG CCT GGC ACC TCA CCT GCT CTG CTG CAG GGG ACA GCA GAG GAA     399
Arg Arg Pro Gly Thr Ser Pro Ala Leu Leu Gln Gly Thr Ala Glu Glu
         95                 100                 105

GAC CAT GTG GAC CTG TCA CTG TCT TGT ACC CTT GTG CCT CGC TCA GGG     447
Asp His Val Asp Leu Ser Leu Ser Cys Thr Leu Val Pro Arg Ser Gly
    110                 115                 120

GAG CAG GCT GAA GGG TCC CCA GGT GGA CCT GGA GAC TCT CAG GGT CGA     495
Glu Gln Ala Glu Gly Ser Pro Gly Gly Pro Gly Asp Ser Gln Gly Arg
125                 130                 135                 140

AAA CGG CGG CAG ACC AGC ATG ACA GAT TTC TAC CAC TCC AAA CGC CGG     543
Lys Arg Arg Gln Thr Ser Met Thr Asp Phe Tyr His Ser Lys Arg Arg
                145                 150                 155

CTG ATC TTC TCC AAG AGG AAG CCC T AATCCGCCCA CAGGAAGCCT             588
Leu Ile Phe Ser Lys Arg Lys Pro
            160

GCAGTCCTGG AAGCGCGAGG GCCTCAAAGG CCCGCTCTAC ATCTTCTGCC TTAGTCTCAG    648

TTTGTGTGTC TTAATTATTA TTTGTGTTTT AATTTAAACA CCTCCTCATG TACATACCCT    708

GGCCGCCCCC TGCCCCCCAG CCTCTGGCAT TAGAATTATT TAAACAAAAA CTAGGCGGTT    768

GAATGAGAGG TTCCTAAGAG TGCTGGGCAT TTTTATTTTA TGAAATACTA TTTAAAGCCT    828

CCTCATCCCG TGTTCTCCTT TTCCTCTCTC CCGGAGGTTG GGTGGGCCGG CTTCATGCCA    888

GCTACTTCCT CCTCCCCACT TGTCCGCTGG GTGGTACCCT CTGGAGGGGT GTGGCTCCTT    948
```

-continued

```
CCCATCGCTG TCACAGGCGG TTATGAAATT CACCCCCTTT CCTGGACACT CAGACCTGAA   1008

TTCTTTTTCA TTTGAGAAGT AAACAGATGG CACTTTGAAG GGGCCTCACC GAGTGGGGGC   1068

ATCATCAAAA ACTTTGGAGT CCCCTCACCT CCTCTAAGGT TGGGCAGGGT GACCCTGAAG   1128

TGAGCACAGC CTAGGGCTGA GCTGGGGACC TGGTACCCTC CTGGCTCTTG ATACCCCCCT   1188

CTGTCTTGTG AAGGCAGGGG GAAGGTGGGG TACTGGAGCA GACCACCCCG CCTGCCCTCA   1248

TGGCCCCTCT GACCTGCACT GGGGAGCCCG TCTCAGTGTT GAGCCTTTTC CCTCTTTGGC   1308

TCCCCTGTAC CTTTTGAGGA GCCCCAGCTT ACCCTTCTTC TCCAGCTGGG CTCTGCAATT   1368

CCCCTCTGCT GCTGTCCCTC CCCCTTGTCT TTCCCTTCAG TACCCTCTCA TGCTCCAGGT   1428

GGCTCTGAGG TGCCTGTCCC ACCCCCACCC CCAGCTCAAT GGACTGGAAG GGGAAGGGAC   1488

ACACAAGAAG AAGGGCACCC TAGTTCTACC TCAGGCAGCT CAAGCAGCGA CCGCCCCCTC   1548

CTCTAGCTGT GGGGGTGAGG GTCCCATGTG GTGGCACAGG CCCCCTTGAG TGGGGTTATC   1608

TCTGTGTTAG GGGTATATGA TGGGGGAGTA GATCTTTCTA GGAGGGAGAC ACTGGCCCCT   1668

CAAATCGTCC AGCGACCTTC CTCATCCACC CCATCCCTCC CCAGTTCATT GCACTTTGAT   1728

TAGCAGCGGA ACAAGGAGTC AGACATTTTA AGATGGTGGC AGTAGAGGCT ATGGACAGGG   1788

CATGCCACGT GGGCTCATAT GGGGCTGGGA GTAGTTGTCT TTCCTGGCAC TAACGTTGAG   1848

CCCCTGGAGG CACTGAAGTG CTTAGTGTAC TTGGAGTATT GGGGTCTGAC CCCAAACACC   1908

TTCCAGCTCC TGTAACATAC TGGCCTGGAC TGTTTTCTCT CGGCTCCCCA TGTGTCCTGG   1968

TTCCCGTTTC TCCACCTAGA CTGTAAACCT CTCGAGGGCA GGGACCACAC CCTGTACTGT   2028

TCTGTGTCTT TCACAGCTCC TCCCACAATG CTGAATATAC AGCAGGTGCT CAATAAATGA   2088

TTCTTAGTGA CTTTAAAAAA AAAAAAAAAA AAA                                2121
```

(2) INFORMATION FOR SEQ ID NO:2:

(i) SEQUENCE CHARACTERISTICS:
(A) LENGTH: 164 amino acids
(B) TYPE: amino acid
(D) TOPOLOGY: linear (ii) MOLECULE TYPE: protein (xi) SEQUENCE DESCRIPTION: SEQ ID NO:2:

```
Met Ser Glu Pro Ala Gly Asp Val Arg Gln Asn Pro Cys Gly Ser Lys
  1               5                  10                  15

Ala Cys Arg Arg Leu Phe Gly Pro Val Asp Ser Glu Gln Leu Ser Arg
             20                  25                  30

Asp Cys Asp Ala Leu Met Ala Gly Cys Ile Gln Glu Ala Arg Glu Arg
         35                  40                  45

Trp Asn Phe Asp Phe Val Thr Glu Thr Pro Leu Glu Gly Asp Phe Ala
     50                  55                  60

Trp Glu Arg Val Arg Gly Leu Gly Leu Pro Lys Leu Tyr Leu Pro Thr
 65                  70                  75                  80

Gly Pro Arg Arg Gly Arg Asp Glu Leu Gly Gly Gly Arg Arg Pro Gly
                 85                  90                  95

Thr Ser Pro Ala Leu Leu Gln Gly Thr Ala Glu Glu Asp His Val Asp
            100                 105                 110

Leu Ser Leu Ser Cys Thr Leu Val Pro Arg Ser Gly Glu Gln Ala Glu
        115                 120                 125

Gly Ser Pro Gly Gly Pro Gly Asp Ser Gln Gly Arg Lys Arg Arg Gln
    130                 135                 140
```

-continued

Thr Ser Met Thr Asp Phe Tyr His Ser Lys Arg Arg Leu Ile Phe Ser
145 150 155 160

Lys Arg Lys Pro (2) INFORMATION FOR SEQ ID NO:3:

(i) SEQUENCE CHARACTERISTICS:
(A) LENGTH: 20 base pairs
(B) TYPE: nucleic acid
(C) STRANDEDNESS: double
(D) TOPOLOGY: linear (ii) MOLECULE TYPE: DNA (genomic)

(iii) HYPOTHETICAL: NO (iv) ANTI-SENSE: NO (vi) ORIGINAL SOURCE:
(A) ORGANISM: Homo sapiens (viii) POSITION IN GENOME:
(A) CHROMOSOME/SEGMENT: 6p21.2

(ix) FEATURE:
(A) NAME/KEY: protein_bind
(B) LOCATION: 1..20
(D) OTHER INFORMATION: /bound_moiety= "p53"

(xi) SEQUENCE DESCRIPTION: SEQ ID NO:3:

GAACATGTCC CAACATGTTG 20

(2) INFORMATION FOR SEQ ID NO:4:

(i) SEQUENCE CHARACTERISTICS:
(A) LENGTH: 136 base pairs
(B) TYPE: nucleic acid
(C) STRANDEDNESS: double
(D) TOPOLOGY: linear (ii) MOLECULE TYPE: DNA (genomic)

(iii) HYPOTHETICAL: NO (iv) ANTI-SENSE: NO (vi) ORIGINAL SOURCE:
(A) ORGANISM: Homo sapiens (viii) POSITION IN GENOME:
(A) CHROMOSOME/SEGMENT: 6p21.2

(xi) SEQUENCE DESCRIPTION: SEQ ID NO:4:

GGGGAGGGAG GTCCCGGGCG GCGTCGGTGG GCCGAGCGCG GGTCCCGCCT CCTTGAGGCG 60

GGCCCGGGCG GGGCGGTTGT ATATCAGGGC CGCGCTGAGC TGCGCCAGCT GAGGTGTGAG 120

CAGCTGCCGA AGTCAG 136

(2) INFORMATION FOR SEQ ID NO:5:

(i) SEQUENCE CHARACTERISTICS:
(A) LENGTH: 23 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (iv) ANTI-SENSE: NO

-continued

```
    (vi) ORIGINAL SOURCE:
          (A) ORGANISM: Homo sapiens

  (viii) POSITION IN GENOME:
          (B) MAP POSITION: 6.21.2

    (xi) SEQUENCE DESCRIPTION: SEQ ID NO:5:

CCACAAGCTT CTGACTTCGG CAG                                              23


(2) INFORMATION FOR SEQ ID NO:6:

     (i) SEQUENCE CHARACTERISTICS:
          (A) LENGTH: 24 base pairs
          (B) TYPE: nucleic acid
          (C) STRANDEDNESS: single
          (D) TOPOLOGY: linear

    (ii) MOLECULE TYPE: DNA (genomic)

   (iii) HYPOTHETICAL: NO

    (iv) ANTI-SENSE: NO

    (vi) ORIGINAL SOURCE:
          (A) ORGANISM: Homo sapiens

  (viii) POSITION IN GENOME:
          (A) CHROMOSOME/SEGMENT: 6.21.2

    (xi) SEQUENCE DESCRIPTION: SEQ ID NO:6:

CCCAGGAACA AGCTTGGGCA GCAG                                             24
```